United States Patent [19]

Diefenbach

[11] 4,364,872

[45] Dec. 21, 1982

[54] METHOD OF MAKING ALUMINUM ALKYLS

[75] Inventor: Steven P. Diefenbach, Baton Rouge, La.

[73] Assignee: Ethyl Corporation, Richmond, Va.

[21] Appl. No.: 282,493

[22] Filed: Jul. 13, 1981

[51] Int. Cl.³ .............................................. C07F 5/06
[52] U.S. Cl. ............................................... 260/448 A
[58] Field of Search .................................... 260/448 A

[56] References Cited

U.S. PATENT DOCUMENTS

| | | | |
|---|---|---|---|
| 2,691,668 | 10/1954 | Liegler et al. | 260/448 A |
| 2,744,127 | 5/1956 | Liegler et al. | 260/448 A |
| 2,839,556 | 6/1958 | Liegler et al. | 260/448 A |
| 2,863,894 | 12/1958 | Smith | 260/448 A |
| 2,931,820 | 4/1960 | Barclay et al. | 260/448 A |
| 4,118,409 | 10/1978 | Eidt et al. | 260/448 A |

*Primary Examiner*—Helen M. S. Sneed
*Attorney, Agent, or Firm*—Donald L. Johnson; John F. Sieberth; Paul H. Leonard

[57] ABSTRACT

A method of making trimethylaluminum wherein an aluminum trialkyl having at least two carbon atoms in the alkyl group is reacted with a methyl halide in the presence of a bismuth catalyst to form trimethylaluminum and an alkyl halide. A hydrocarbon solvent provides increased reaction rates.

22 Claims, No Drawings

METHOD OF MAKING ALUMINUM ALKYLS

BACKGROUND OF THE INVENTION

Field of the Invention

The present invention relates to a method of making aluminum alkyls or alkyl aluminum compounds and especially to the making of trimethylaluminum.

A variety of processes are known for the preparation of aluminum alkyls and for the preparation of trimethylaluminum in particular. Decomposition reactions of aluminum alkyls with alkyl halides are documented in the literature.

One preferred method for making trimethylaluminum involves the sodium reduction of methylaluminum sesquichloride. Such procedure is an expensive one. Processes of this type are described in British Pat. No. 762,200 and U.S. Pat. No. 2,954,389 and in an article by A. V. Grosse and J. M. Mavity, *Journal of Organic Chemistry*, 5, 106 (1940). Preparation of trimethylaluminum has also been carried out by the sodium reduction of dimethylaluminum chloride as described in an article by S. Pasynkiewicz and M. Boleslawski, *Journal of Organometallic Chemistry*, 25, 29 (1970). The methods described in the foregoing articles each form a basis for existing economical commercial processes for the production of trimethylaluminum, but each produce non-usable by-products having limited value in vast quantities in comparison to the trimethylaluminum produced. The by-products produced by the above processes are aluminum and sodium chloride.

The several processes that have utilized the above sodium retention reactions suffer from an inherent problem in that trimethylaluminum will itself react with sodium to produce sodium tetramethylaluminate, a compound that, unless it reacts with dimethylaluminum chloride will cause reduced yields and present a disposal problem. Sodium tetramethylaluminate is extremely reactive towards moisture in the air, as also would be excess unreacted sodium. The disposal problems presented by these two compounds represent a significant proportion of the cost of production of trimethylaluminum manufactured by such processes.

Although the conversion of dimethylaluminum chloride to trimethylaluminum without the use of sodium (Cryolite Process) is described in U.S. Pat. No. 2,839,556, this reaction scheme produces a vast amount of solid by-product having limited commercial value.

Two other methods for production of aluminum trialkyls are described in an article by R. Koster and P. Binger, *Advances in Inorganic and Radiochemistry*, I, 1263 (1965) and by K. S. Pitzer and H. S. Gutowsky, *Journal of American Chemical Society*, 68, 2204 (1946). Both of these methods suffer from the use of expensive starting materials and the production of non-useful or extremely reactive by-products requiring expensive process equipment and handling techniques.

U.S. Pat. No. 2,744,127 describes a relatively simple process for the preparation of trimethylaluminum which produces as a by-product magnesium chloride in the weight ratio 2.7:1 magnesium chloride:trimethylaluminum. The magnesium chloride has little or no commercial value.

A process for producing a mono-hydrocarbon aluminum dihalide is disclosed in U.S. Pat. No. 2,270,292. In such process, a hydrocarbon halide is reacted with metallic aluminum to form a dihydrocarbon-aluminum-monohalide and the latter is then reacted with an aluminum trihalide to form the desired dihalide product.

U.S. Pat. No. 2,863,894 relates to a process for producing aluminum alkyls, wherein aluminum is reacted with a primary alkyl halide, including methyl iodide in the presence of an inert, aromatic-free solvent to form a solution of sesquihalide dissolved in the inert solvent and then reacting the sesquihalide with an alkali metal to form the aluminum alkyl.

A more recent patent, U.S. Pat. No. 4,118,409, provides for jointly making trimethylaluminum and alkylaluminum bromides and iodides by mixing an aluminum trialkyl and a methylaluminum bromide or iodide and then distilling from the mixture trimethylaluminum as a first fraction and then alkylaluminum bromides or iodides as a subsequent fraction. The alkylaluminum halides used in such a redistribution process are themselves expensive compounds.

SUMMARY OF THE INVENTION

The present invention relates to a process for making trimethylaluminum, wherein a trialkylaluminum having at least two carbon atoms in the alkyl group is reacted with methyl halide in the presence of a bismuth-based or bismuth component catalyst to form trimethylaluminum and an alkyl halide.

An alkyl group exchange reaction occurs between the trialkylaluminum reactant, preferably, triethylaluminum and the methyl halide, preferably, methyl bromide. When using methyl bromide as the methyl halide reactant and bismuth trichloride as the bismuth component of the catalyst, the experimental evidence indicates that the catalytic species may involve a viscous oil composed of bismuth, aluminum, and chloride and methyl groups.

An advantage of this invention is that the exchange reaction can be conducted under conditions whereby the reaction is complete after one hour while achieving yields via NMR (Nuclear Magnetic Response) of 95 percent or higher of trimethylaluminum and ethyl bromide.

While similar exchange reaction between trimethylaluminum and methyl chloride can be effected, the reaction is not as clean as the one with methyl bromide. Side reactions may occur between the aluminum alkyls and methyl chloride which result in the formation of hydrocarbon co-products, e.g., methane, ethane and propane and alkylaluminum chlorides.

The active catalyst may be prepared in situ or separately by first reacting a slurry of a suitable bismuth compound, preferably, bismuth chloride ($BiCl_3$) or triphenyl bismuth, in decane or other hydrocarbon solvent with a trialkylaluminum compound such as triethylaluminum. The stoichiometry of the reaction is not well defined. Heating of the resulting solution in the presence of methyl bromide or methyl chloride appears to afford the active catalyst species. Evaporation of excess alkyl halides causes most of the catalyst to separate from the hydrocarbon solvent as a clear, dense, almost colorless oil. This enables the catalyst to be isolated and recycled after the exchange reaction is complete. The last traces of bismuth may be removed by distillation of the trimethylaluminum.

DESCRIPTION OF THE PREFERRED EMBODIMENTS

In the preferred form of the invention, trimethylaluminum is prepared by a catalyzed alkyl group exchange reaction between trialkylaluminum and a methyl halide. The following equation represents the reaction:

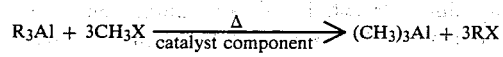

$$R_3Al + 3CH_3X \xrightarrow[\text{catalyst component}]{\Delta} (CH_3)_3Al + 3RX$$

wherein
R=C$_2$H$_5$ to C$_4$H$_9$
X=Br or Cl
Catalyst component=a bismuth compound which is capable of forming an alkyl-bismuth bond in the reaction.

The catalyst components that may be used in the instant invention are alkyl or aryl bismuth compounds or an inorganic bisumth salt which can be converted in situ to an alkyl bismuth or aryl bismuth. Any bismuth compound may be used which is capable of forming an alkyl bismuth bond or an aryl bismuth bond in the reaction. Only a small amount of the bismuth compound is required. The amount should be sufficient to provide the desired reaction rate.

Triphenyl bismuth [Bi(C$_6$H$_5$)$_3$] and bismuth chloride (BiCl$_3$) are preferred bismuth compounds as a catalyst component. Other bismuth halides such as bismuth bromide (BiBr$_3$) and bismuth iodide (BiI$_3$) may also be used as catalyst components. Additional suitable catalyst components are alkyl bismuths such as triethyl bismuth and trimethyl bismuth.

The most preferred catalyst is prepared in situ by reacting a slurry of bismuth chloride in a hydrocarbon solvent with approximately an equimolar quantity of triethylaluminum. The catalyst can also be formed with trimethylaluminum.

The amount of bismuth-based or bismuth component catalyst employed is susceptible to variation. Amounts of as little as one or two mole percent and as high as 25 mole percent, based on initial concentration of triethylaluminum may be used. Small amounts require long reaction times. In general, the higher the catalyst concentration, the faster the reaction proceeds. The amount of the catalyst may be tailored to provide a desired reaction time. In a preferred embodiment, about 2.28 mole percent of the bismuth-based catalyst is used with excess methyl bromide and the reaction is carried out at about 115° C. for about 1 hour.

No solvent is required in the present invention; however, increased reaction rates are observed when a solvent is used. The preferred solvents are aliphatic hydrocarbons, both cyclic and acyclic. Cyclohexane and decane each provided excellent yields. Aromatic hydrocarbons may also be used provided they do not alkylate under reaction conditions.

Ordinarily, reaction temperatures will fall in the range of about 50° C. to about 150° C. Some variation from this range may be permissible. A temperature of 90° C. provides a reasonable reaction rate. Higher temperatures, up to about 115° C., substantially decrease the reaction time. Increased catalyst concentration also decreases reaction time. In general, temperature and catalyst concentration can be varied to achieve desired reaction rate.

Excess methyl halide and by-product ethyl halide are distilled from the homogeneous reaction mixture leaving two liquid layers. The upper layer which is trimethylaluminum in decane is separated from the lower layer and can be distilled to recover pure trimethylaluminum. The lower layer contains the active catalyst and may be recycled for the next run. Decane remains in the bottoms from the distillation of trimethylaluminum and can also be recycled.

The foregoing described invention can be further understood by the following examples:

GENERAL

Reactants used were commercially available products and were used as received unless otherwise noted. Methyl chloride and all aluminum alkyls compounds were products of Ethyl Corporation. Methyl bromide was obtained from Matheson. Bismuth trichloride and triphenyl bismuth were purchased from Alfa Division, Ventron Corporation. All reactants were stored in a nitrogen-filled dry box. Cyclohexane was deoxygenated and stored over molecular sieves. NMR spectra were recorded on a Varian EM-390 90 MHz spectrometer. All manipulations were performed in a nitrogen-filled dry box.

General Procedure for the Triethylaluminum-Methyl Bromide Alkyl Group Exchange Reaction—Catalyst Formed In Situ The general procedure for the catalytic alkyl group exchange reactions (Tables I–IV) consists of charging a Fisher-Porter pressure vessel in a nitrogen-filled dry box with the indicated quantities of catalyst, solvent, if used, and triethylaluminum. With triphenyl bismuth, there was no noticeable reaction upon addition of triethylaluminum. When bismuth trichloride was used as the catalyst, the addition of triethylaluminum had to be carried out dropwise until a finely divided grey solid and clear solution resulted. At this point, the remaining triethylaluminum could be added all at once. The reaction can be conducted with or without the grey solid present. In runs where cyclohexane was absent, a few mole percent was added as an internal NMR standard. In most runs, cyclohexane functioned as solvent and standard. At this point, the NMR spectrum of the initial reaction solution was taken. The vessel was then capped with a plug containing a pressure gauge, thermocouple well, pressure relief valve, and dip leg. The vessel was removed from the dry box and cooled to −78° C. Cooling is a convenient means for simplifying handling. Any suitable temperature may be used. The appropriate quantity of methyl bromide was charged into the vessel. After warming to room temperature, the vessel was placed into an oil bath, warmed to the desired temperature and heated at this temperature for the appropriate length of time. The vessel was cooled in dry ice and then transferred to the dry box for work-up. Excess gases were vented. An ~1 ml aliquot of the clear, colorless reaction mixture was filtered through a Millipore Swinnex filter disc containing a Mitex filter into an NMR tube. The NMR spectrum was recorded and the yield of methyl groups were calculated versus the internal cyclohexane standard. In runs where cyclohexane or decane was used as a solvent, it was possible to separate the catalyst from the product by simply bubbling a stream of nitrogen slowly through the reaction mixture to evaporate methyl bromide and ethyl bromide. Once most of the alkyl bromides had been evaporated, a clear oil with a brownish-yellow tint separated from the hydrocarbon solution. The two layers can be separated by simply syringing off the top layer. In this manner, the lower catalyst layer may be recycled.

Procedure for Separate Preparation of Catalyst Oil

The catalyst oil can be prepared separately by charging a Fisher-Porter pressure vessel with 4.0 ml cyclohexane and 1.6 g (5 mmoles) bismuth trichloride. To the white slurry was added dropwise 2.0 ml (14.6 mmoles) triethylaluminum. A grey solid and pale yellow solution resulted. The yellow solution precipitated a white solid while standing overnight in the dry box. To this mixture was added another 1.4 ml (10.2 mmoles) of triethylaluminum. The additional triethylaluminum reacted to give a grey solid and clear solution. The grey solid was filtered off and the filtrate was placed into a clean vessel. The vessel was then capped and removed from the dry box. The vessel was cooled to −78° C. before charging with 5 g (5 mmoles) methyl bromide. After warming to room temperature, the vessel was heated at 115° C. for 1.0 hour. After cooling to room temperature, the vessel was placed into the dry box. Excess gases were vented. Upon slow evaporation of ethyl bromide and excess methyl bromide under a stream of nitrogen, two liquid layers separated. The top cyclohexane layer consisted of trace amounts of methyl bromide, ethyl bromide and trimethylaluminum (NMR). This layer was removed with a syringe. The bottom layer, the catalyst, consisted of a viscous oil. The oil was clear and nearly colorless. A very small amount of white solid was also present. The NMR spectrum of the oil showed two broad singlets at ~0 ppm and ~3.0 ppm and a small amount of ethyl bromide. The white solid was not investigated.

The catalyst oil can also be prepared from a similar reaction between trimethylaluminum, bismuth trichloride and methyl bromide in cyclohexane solvent. The NMR spectrum of the oil prepared from trimethylaluminum was identical to the spectrum obtained from triethylaluminum.

Procedure for the Triethylaluminum-Methyl Bromide Exchange Reaction Using a Preformed Catalyst The oil isolated from the above preparation was charged into a Fisher-Porter pressure vessel containing 4.0 ml of cyclohexane. The oil settled to the bottom. To this mixture was added 3.0 ml (21.9 mmoles) triethylaluminum. The vessel was then charged with 40 g (400 mmoles) of methyl bromide and heated at 115° for 2 hours. The vessel was cooled in dry ice, then placed into the dry box. Excess gases were vented. Dissolved methyl bromide and ethyl bromide were slowly evaporated under a stream of nitrogen until two layers were present. An ~1 ml aliquot of the top cyclohexane layer was filtered into an NMR tube. The NMR spectrum showed almost a quantitative conversion to trimethylaluminum.

General Procedure for the Triethylaluminum-Methyl Chloride Exchange Reactions (Table V)

A 200 ml flask was charged with 30 ml of decane and 10.24 g (32 mmoles; 24.4 mole %) of bismuth trichloride. To the white slurry was slowly added 4.0 ml of triethylaluminum. A clear, colorless solution containing a grey precipitate resulted. To this mixture was added an additional 14.0 ml (18.0 ml total; 132 mmoles) of triethylaluminum. The clear solution was removed with a syringe and placed into a 300 ml autoclave. The grey solid can be filtered off or included in the solution. The autoclave was then charged with 60 g (~1200 mmoles) of methyl chloride. The temperature of the reaction mixture was slowly raised to 100° C. (1.0 hour) then held at this temperature for 1.0–2.5 hours. The pressure of the autoclave reached a maximum of 400 psig. After allowing the autoclave to cool to room temperature, the excess gases were vented in the hood. In Runs 3 and 4, an aliquot of this gas was collected in a gas sampling bottle for gas chromatography (g.c.) (Table VI). The autoclave was then placed into the dry box and opened. The contents were poured into a wide mouth jar. Two phases were present. Nitrogen was slowly bubbled through the mixture to remove the alkyl halides from the product layer. This procedure was necessary because the alkyl halides substantially increased the solubility of the catalyst in the product layer. The two layers could be separated adequately by syringing off the top layer. An aliquot of the top layer was filtered into an NMR tube. The NMR spectrum indicated the top layer consisted of decane and alkylaluminum compounds. From the spectrum, it was possible to obtain the $CH_3:C_2H_5$ ratio. A reaction time of >1.75 hours at 100° C. was necessary to completely consume the initial triethylaluminum.

The results of experimental runs using the foregoing procedures are summarized in Tables I through VI.

TABLE I

Triethylaluminum-Methyl Bromide Catalytic Exchange Reactions
$Et_3Al + 3MeBr \rightarrow Me_3Al + 3EtBr^a$

| Run No. | $Et_3Al$ (mmoles) | MeBr (mmoles) | mmole Catalyst (mole percent) | Conditions (Solv) | Percent Exchange[b] |
|---|---|---|---|---|---|
| 1 | 21.9 | 100 | 0.5 $Ph_3Bi^a$ (2.28) | 90° C., 18 hrs | 100 |
| 2 | 21.9 | 100 | 0.5 $Ph_3Bi$ (2.28) | 90° C., 16 hrs | 95 |
| 3 | 21.9 | 100 | 0.5 $BiCl_3$ (2.28) | 90° C., 18 hrs ($C_6H_{12}$) | 100 |
| 4 | 21.9 | 100 | 0.25 $Ph_3Bi$ (1.14) | 25° C., 66 hrs | N.R. |
| 5 | 65.7 | 200 | 0.5 $Ph_3Bi$ (0.76) | 90° C., 22 hrs | 100 |
| 6[c] | 21.9 | 100 | 0.5 $Ph_3Bi$ (2.28) | 90° C., 18 hrs | 100 |
| 7 | 44.0 | 200 | Same | 90° C., 18 hrs | 100 |
| 8[d] | 14.6 | 50 | 5.0 $BiCl_3$ | 115° C., 1.0 hr | 100 |
| 9[e] | 21.9 | 400 | Oil-$BiCl_3$ | 115° C., 2.0 hrs | 90 |
| 10[f] | 21.9 | 300 | Oil-$BiCl_3$ | 115° C., 1.5 hrs | 90 |
| 11 | 44.0 | 300 | 2.0 $BiCl_3$ (4.54) | 115° C., 2.5 hrs | 100 |

TABLE I-continued

Triethylaluminum-Methyl Bromide Catalytic Exchange Reactions
$Et_3Al + 3MeBr \rightarrow Me_3Al + 3EtBr^a$

| Run No. | $Et_3Al$ (mmoles) | MeBr (mmoles) | mmole Catalyst (mole percent) | Conditions (Solv) | Percent Exchange[b] |
|---|---|---|---|---|---|
| | | | | $(C_{10}H_{22})$ | |

[a] Et = ethyl; Me = methyl; Ph = phenyl
[b] The percent exchange was calculated from the NMR integration vs a cyclohexane standard.
[c] In this experiment, two cycles were made with the initial catalyst mix. Upon completion of cycle one, the indicated amounts of $Et_3Al$ and MeBr were then added directly to the charge for the start of cycle two.
[d] This run was a separate catalyst preparation.
[e] The catalyst used in this run was prepared separately from Run 8
[f] The catalyst used in this run was prepared separately from the reaction between $Me_3Al$, $BiCl_3$ and MeBr.

TABLE II $Et_3Al$-MeBr Catalytic Exchange Reactions - Percent Exchange vs. [MeBr]

| Run No. | $Et_3Al$ (mmoles) | MeBr (mmoles) | Catalyst Mol % $BiCl_3$ | $C_6H_{12}$ (ml) | hr/°C. | Percent Exchange[a] |
|---|---|---|---|---|---|---|
| 1 | 21.9 | 100 | 2.28 | 1.0 | 1.0/115 | 61 |
| 2 | 21.9 | 200 | 2.28 | 1.0 | 1.0/115 | 53 |
| 3 | 21.9 | 300 | 2.28 | 1.0 | 1.0/115 | 67 |

[a] The percent exchange was calculated from the NMR integration vs a cyclohexane standard.

TABLE III $Et_3Al$-MeBr Catalytic Exchange Reactions - Percent Exchange vs. [Catalyst]

| Run No. | $Et_3Al$ (mmoles) | MeBr (mmoles) | Catalyst mol % $BiCl_3$ | $C_6H_{12}$ (ml) | hr/°C. | Percent Exchange[a] |
|---|---|---|---|---|---|---|
| 1 | 21.9 | 100 | 1.14 | 1.0 | 1.0/115 | 34 |
| 2 | 21.9 | 100 | 2.28 | 1.0 | 1.0/115 | 61 |
| 3 | 21.9 | 100 | 4.56 | 1.0 | 1.0/115 | >95 |
| 4 | 21.9 | 100 | 9.13 | 1.0 | 1.0/115 | >95 |

[a] The percent exchange was calculated from the NMR integration vs a cyclohexane standard.

TABLE IV $Et_3Al$-MeBr Catalytic Exchange Reactions - Percent Exchange vs. $[C_6H_{12}]$

| Run No. | $Et_3Al$ (mmoles) | MeBr (mmoles) | Catalyst mol % $BiCl_3$ | $C_6H_{12}$ (ml) | hr/°C. | Percent Exchange[a] |
|---|---|---|---|---|---|---|
| 1 | 21.9 | 100 | 2.28 | 0 | | 25 |
| 2 | 21.9 | 100 | 2.28 | 1.0 | 1.0/115 | 61 |
| 3 | 21.9 | 100 | 2.28 | 3.0 | 1.0/115 | >95 |
| 4 | 21.9 | 100 | 2.28 | 5.0 | 1.0/115 | >95 |

[a] The percent exchange was calculated from the NMR integration vs a cyclohexane standard.

TABLE V

Triethylaluminum-Methyl Chloride Catalytic Exchange Reactions
$Et_3Al + 3MeCl \rightarrow Me_3Al + 3EtCl$

| Run No. | $Et_3Al$ (mmoles) | MeCl (mmoles) | mmol Catalyst (mol %) | Conditions | Solvent (ml) | Me:Et[a] |
|---|---|---|---|---|---|---|
| 1 | 132 | 1200 | 8.0 $BiCl_3$ (6.1) | 100°/1.0 h | decane (30) | 25:75 |
| 2 | 132 | 1200 | 16.0 $BiCl_3$ (12.2) | 100°/2.5 h | decane (30) | 70:30 |
| 3 | 132 | 1200 | 32.0 $BiCl_3$ (24.4) | 100°/1.75 h | decane (30) | 100:0 |
| 4 | 132 | 1200 | Oil from Run 3 | 100°/2.5 h | decane (30) | 86:13 |

[a] Ratio of methyl groups to ethyl groups that are bonded to aluminum.

TABLE VI $Et_3Al$-MeCl Catalytic Exchange Reactions - Representative G.C. Analysis of Gas Above the Final Reaction Mixture

| Components | Normalized Mole Percent |
|---|---|
| $N_2$ plus air | 9.99 |

TABLE VI-continued $Et_3Al$-MeCl Catalytic Exchange Reactions - Representative G.C. Analysis of Gas Above the Final Reaction Mixture

| Components | Normalized Mole Percent |
|---|---|
| $CH_4$ | 12.7 |
| $C_2H_6$ | 12.9 |
| $C_2H_4$ | .53 |
| $C_3H_8$ | 3.68 |
| $C_3H_6$ | .01 |
| $i-C_4H_{10}$ | .02 |
| $n-C_4H_{10}$ | .68 |
| MeCl | 55.4 |
| $i-C_5H_{12}$ | .01 |
| $n-C_5H_{12}$ | .01 |
| EtCl | 4.13 |
| $C_6H_{14}$ | ~.005 |
| $C_7H_{16}$ | ~.005 |

It was also possible to use the isolated catalyst oil for the $Et_3Al$—MeCl exchange. This was accomplished by first adding the oil to a solution of 132 mmoles $Et_3Al$ in 30 ml decane, then charging the autoclave with 1200 mmoles MeCl. The autoclave was slowly heated to 100° C. (1 hour), then held at the temperature for 2.5 hours. After cooling to room temperature, the reaction was worked up as described for the other runs.

While the foregoing disclosure deals primarily with the use of methyl chloride and most preferably methyl bromide as the methyl halide reactant, it will be understood that methyl iodide may be used in the process. In copending application Ser. No. 282,495, filed even date herewith, it is shown that methyl iodide does not require a catalyst in effecting the exchange reaction. However, in the absence of an added catalyst, reaction times generally tend to be in the range of 18 to 24 hours.

The foregoing disclosure and description of the invention are illustrative and explanatory thereof, and various changes may be made within the scope of the appended claims without departing from the spirit of the invention.

I claim:

1. A method of effecting an alkyl exchange reaction, comprising reacting trialkylaluminum having at least two carbon atoms in the alkyl group with methyl halide in the presence of a bismuth-based catalyst to form an alkyl halide having at least two carbon atoms and an alkyl aluminum product containing at least some aluminum to methyl bonds, said bismuth-based catalyst comprising a bismuth compound which is capable of forming an alkyl bismuth bond or an aryl bismuth bond in the reaction.

2. The method of claim 1, wherein the methyl halide is selected from the group consisting of methyl chloride and methyl bromide.

3. The method of claim 1, wherein the methyl halide is methyl bromide.

4. The method of claim 1, wherein the methyl halide is methyl chloride.

5. The method of claim 1, wherein the bismuth compound is a bismuth trihalide.

6. The method of claim 1, wherein the bismuth compound used is bismuth trichloride.

7. The method of claim 1, wherein the bismuth compound used is a trihydrocarbyl bismuth compound.

8. The method of claim 1, wherein the bismuth compound used is triphenyl bismuth.

9. A method of making trimethylaluminum, comprising the following catalyzed exchange reaction:

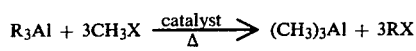

wherein
R = C$_2$–C$_4$ alkyl group
X = bromine or chlorine

Catalyst includes bismuth trichloride or triphenyl bismuth or bismuth trihalide.

10. The method of claim 9, wherein R is an ethyl group.

11. The method of claim 9, wherein X is bromine.

12. The method of claim 9, wherein X is chlorine.

13. The method of claim 1, wherein the reaction is carried out at a temperature of from about 50° C. to about 150° C.

14. The method of claim 1, wherein the reaction is carried out at a temperature of about 100°–115° C.

15. The method of claim 1, wherein the reaction is carried out in up to about 24 hours.

16. The method of claim 1, wherein the reaction is carried out in the presence of a hydrocarbon solvent which does not alkylate with either the aluminum alkyl compounds or the alkyl halides.

17. The method of claim 16, wherein the hydrocarbon solvent is a cyclic or acyclic aliphatic.

18. The method of claim 16, wherein the hydrocarbon solvent is cyclohexane or decane.

19. The method of claim 1, wherein the reaction is carried out at a temperature of at least about 90° C.

20. A method of making trimethylaluminum, comprising reacting triethylaluminum and methyl bromide in the presence of a bismuth chloride or triphenyl bismuth catalyst at a temperature of about 115° C. for at least one hour.

21. The method of claim 1, wherein said trialkylaluminum is triethylaluminum.

22. The method of claim 1, wherein said trialkylaluminum is triethylaluminum and said methyl halide is methyl bromide.

* * * * *

UNITED STATES PATENT AND TRADEMARK OFFICE
CERTIFICATE OF CORRECTION

PATENT NO. : 4,364,872
DATED : December 21, 1982
INVENTOR(S) : Steven P. Diefenbach It is certified that error appears in the above-identified patent and that said Letters Patent is hereby corrected as shown below:

Column 1, line 27 reads "existing economical commercial"
and should read -- existing commercial --.

Column 1, line 34 reads "sodium retention reactions"
and should read -- sodium reduction reactions --.

Column 2, line 39 reads "Magnetic Response)"
and should read -- Magnetic Resonance) --.

Column 6, line 28 reads "in a gas . sampling"
and should read -- in a gas sampling --.

On the cover page of the patent, under References Cited, change the name of the patentee "Liegler et al" to read, -- Ziegler et al -- in all three instances.

Signed and Sealed this

Seventeenth Day of May 1983

[SEAL]

Attest:

DONALD J. QUIGG

Attesting Officer

Acting Commissioner of Patents and Trademarks